(12) United States Patent
Watanabe

(10) Patent No.: US 7,919,102 B2
(45) Date of Patent: Apr. 5, 2011

(54) BASIDIOMYCETES, BASIDIOMYCETES EXTRACT COMPOSITION, HEALTH FOODS, AND IMMUNOPOTENTIATORS

(75) Inventor: Tetsuo Watanabe, Shirone (JP)

(73) Assignee: Mycology Techno. Corp., Niigata (JP)

( * ) Notice: Subject to any disclaimer, the term of this patent is extended or adjusted under 35 U.S.C. 154(b) by 141 days.

(21) Appl. No.: 12/370,206

(22) Filed: Feb. 12, 2009

(65) Prior Publication Data

US 2009/0155300 A1    Jun. 18, 2009

Related U.S. Application Data

(62) Division of application No. 10/554,908, filed as application No. PCT/JP2004/006418 on May 6, 2004, now Pat. No. 7,517,682.

(30) Foreign Application Priority Data

May 1, 2003   (JP) .................................. 2003-126267

(51) Int. Cl.
*A61K 36/07*   (2006.01)
*A61K 36/06*   (2006.01)
*A01N 63/04*   (2006.01)

(52) U.S. Cl. ................. 424/195.15; 435/254.1; 435/911

(58) Field of Classification Search .................. None
See application file for complete search history.

(56) References Cited

U.S. PATENT DOCUMENTS 5,430,055 A    7/1995   Dabrah et al.
6,726,911 B1 *  4/2004   Julich et al. ............... 424/195.15

FOREIGN PATENT DOCUMENTS

| | | | |
|---|---|---|---|
| CN | 1286925 | * | 3/2001 |
| EP | 0 111 631 | | 6/1984 |
| EP | 0 733 647 | | 10/1996 |
| EP | 0 939 082 | | 8/1999 |
| GB | 1 356 449 | | 6/1974 |
| JP | 63-192379 | | 8/1988 |
| JP | 08-023808 | | 1/1996 |
| JP | 11-152230 | | 6/1999 |
| JP | 11-262329 | | 9/1999 |
| JP | 2000-191545 | | 7/2000 |
| JP | 2001-106637 | | 4/2001 |
| JP | 2001-178448 | | 7/2001 |
| JP | 2001-269163 | | 10/2001 |
| JP | 2001-278805 | | 10/2001 |
| JP | 2001-321191 | | 11/2001 |
| KR | 2002012391 | * | 2/2002 |

OTHER PUBLICATIONS

Kanda et al, *Molecular and General Genetics*, 216(2-3):526-529 (1989).
Shaffer et al, *Mycologia*, 67(1):1-18 (1975).

* cited by examiner

*Primary Examiner* — Vera Afremova
(74) *Attorney, Agent, or Firm* — Sughrue Mion, PLLC

(57) ABSTRACT

Basidiomycetes which is a novel mushroom having an excellent immunopotentiating action, etc., a Basidiomycetes extract composition, and health foods and immunopotentiators using the Basidiomycetes extract composition are provided.

Basidiomycetes has no basidium forming potential. In particular, Basidiomycetes is Basidiomycetes-X FERM BP-10011. A Basidiomycetes extract composition is extracted from them with an extraction solvent including at least one solvent selected from water and a hydrophilic solvent.

10 Claims, 3 Drawing Sheets

BASIDIOMYCETES, BASIDIOMYCETES EXTRACT COMPOSITION, HEALTH FOODS, AND IMMUNOPOTENTIATORS

CROSS-REFERENCE TO RELATED APPLICATION

This application is a Divisional of U.S. application Ser. No. 10/554,908, filed Oct. 31, 2005 now U.S. Pat. No. 7,517,682 (now allowed); which is a 371 of PCT/JP2004/006418, filed May 6, 2004; the disclosures of each of which are incorporated herein by reference.

TECHNICAL FIELD

This invention relates to Basidiomycetes which is a novel mushroom (mushroom and other fungi will be collectively referred to hereinafter as mushroom) and has properties such as an immunomodulating effect, a Basidiomycetes extract composition, and health foods and immunopotentiators using the Basidiomycetes extract composition.

BACKGROUND ART

Mushrooms have been used frequently since olden days as food materials having unique flavors and odors. They have also been used as Chinese herbal medicines as having physiological function activating actions, such as enhancement of immunocompetence, antimicrobial activity, control of biorhythm, and prevention of senescence, or as folk medicines for certain types of diseases. Studies of pharmacological ingredients concerned with mushrooms are in progress, resulting in the discovery of ingredients showing antibacterial and antiviral actions, a cardiotonic action, a hypoglycemic action, a cholesterol lowering action, an antithrombotic action, and an antihypertensive action.

Proposals have been made for compositions which are usable as medicines, health foods, etc. and which comprise a mixture of dry products or extracts of two or more mushrooms selected from edible mushrooms among basidiomycetes, especially, *Lentinus edodes* (Berk.) Sing., *Pleurotus ostreatus* (Jacq. ex Fr.) Quel., *Pholiota nameko* (T. Ito) S. Ito et Imai, *Grifola frondosa, Flammulina velutipes* (Curt. ex Fr.) Sing., and *Hypsizigus marmoreus* (see Japanese Patent Application Laid-Open No. 1999-152230).

In recent years, *Agaricus Blazei murill* (hereinafter referred to as *agaricus* mushroom), *Phellinus linteus* (Berk. et Curt) Tehg (hereinafter referred to as mesimacobu) and so on have attracted attention as having an anticancer action.

For examples, proposals have been put forward for a method for high-yield cultivation of mushrooms of the genus *Phellinus* such as mesimacobu (see Japanese Patent Application Laid-Open No. 1999-262329), a method for culturing mesimacobu mycelia for obtaining large amounts of mycelia of mesimacobu (see Japanese Patent Application Laid-Open No. 2001-178448) and a method for efficiently extracting ingredients contained in agaricus mushroom by use of ultrasonic waves (see Japanese Patent Application Laid-Open No. 2001-278805).

As described above, various mushrooms have drawn attention as having an anticancer action, etc. However, they are not decisively effective, and the advent of mushrooms having a better effect is desired.

DISCLOSURE OF THE INVENTION

The present invention has been accomplished in the light of the above-mentioned circumstances. It is an object of the present invention to provide Basidiomycetes which is a novel mushroom having an excellent immunopotentiating action, etc., a Basidiomycetes extract composition, and health foods and immunopotentiators using the Basidiomycetes extract composition.

A first aspect of the present invention, for attaining the above object, lies in Basidiomycetes characterized by having no basidium forming potential.

A second aspect of the present invention lies in the Basidiomycetes of the first aspect, characterized in that the Basidiomycetes is Basidiomycetes-X FERM BP-10011.

A third aspect of the present invention lies in a Basidiomycetes extract composition characterized by being extracted from Basidiomycetes, which has no basidium forming potential, with an extraction solvent including at least one solvent selected from water and a hydrophilic solvent.

A fourth aspect of the present invention lies in the Basidiomycetes extract composition of the third aspect, characterized in that the Basidiomycetes is Basidiomycetes-X FERM BP-10011.

A fifth aspect of the present invention lies in the Basidiomycetes extract composition of the third or fourth aspect, characterized in that the Basidiomycetes extract composition is obtained by heating and extraction.

A sixth aspect of the present invention lies in the Basidiomycetes extract composition of any one of the third to fifth aspects, characterized in that the Basidiomycetes extract composition is obtained by pressurization and extraction.

A seventh aspect of the present invention lies in a health food characterized by containing, as an active ingredient, a Basidiomycetes extract composition extracted from Basidiomycetes having no basidium forming potential.

An eighth aspect of the present invention lies in the health food of the seventh aspect, characterized in that the Basidiomycetes is Basidiomycetes-X FERM BP-10011.

A ninth aspect of the present invention lies in the health food of the seventh or eighth aspect, characterized in that the health food is in a form selected from a drink form, a snack form, a concentrated extract form, a powder, granules, tablets, and capsules.

A tenth aspect of the present invention lies in an immunopotentiator characterized by containing, as an active ingredient, a Basidiomycetes extract composition extracted from Basidiomycetes having no basidium forming potential.

An eleventh aspect of the present invention lies in the immunopotentiator of the tenth aspect, characterized in that the Basidiomycetes is Basidiomycetes-X FERM BP-10011.

A twelfth aspect of the present invention lies in edible Basidiomycetes comprising a hypha mass formed by culturing the Basidiomycetes of the first or second aspect.

Basidiomycetes-X of the present invention described above contains large amounts of polysaccharides (β-D-glucan) and has high antioxidant activity, OH radical elimination activity, and an immunomodulating effect. This organism is preferred when used in health foods and immunopotentiators which can be expected to exhibit pharmacological efficacy, such as prevention of senescence.

BEST MODE FOR CARRYING OUT THE PRESENT INVENTION

Figure 1:
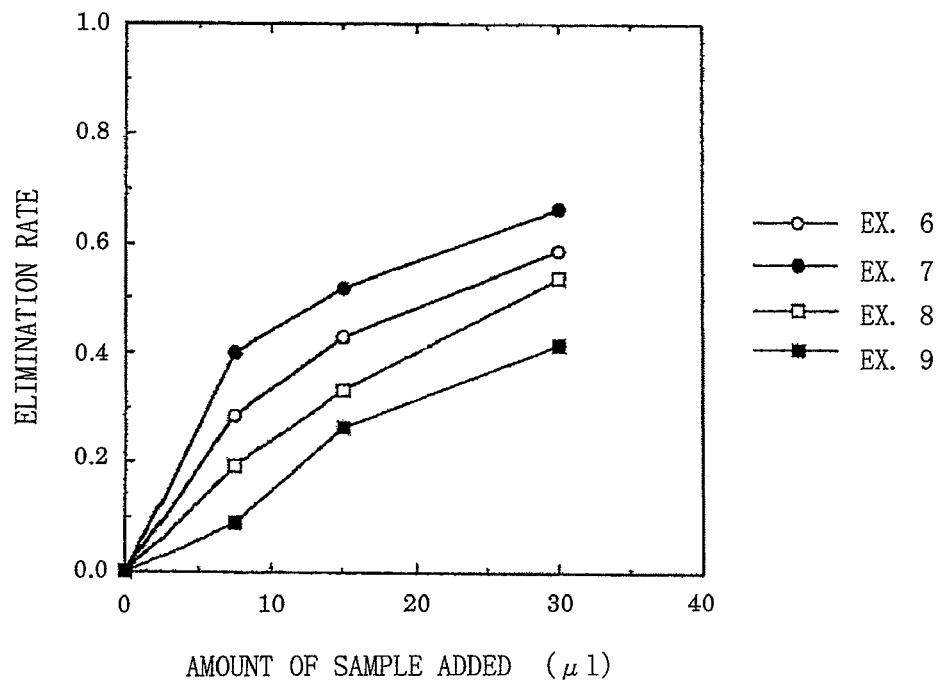
FIG. 1 is a view showing the results of measurements in Test Example 1.

Basidiomycetes, referred to in the present invention, is a basidiomycete, and has properties such that it has no basidium forming potential, although beak-shaped processes (clamps) are observed. In these respects, this basidiomycete is distinguished from other basidiomycetes. That is, even when cultured, Basidiomycetes does not form basidia, and only forms sclerotia (hypha masses).

Such Basidiomycetes was obtained as a result of search for microorganisms in the natural world. It was isolated, and deposited with International Patent Organism Depositary, National Institute of Advanced Industrial Science and Technology, Chuo Dai-6, Higashi 1-1-1, Tsukuba City, Ibaragi Prefecture, Japan 305-8566, as Basidiomycetes-X (Accession No.: FERM BP-100 µl), under the terms of the Budapest Treaty.

The organism according to the present invention forms no conidia, namely, has no asexual generation.

That is, when this organism is cultured on a potato glucose agar medium, cultured hyphae have clamps, and are smooth, but form no conidia, and form no fruit bodies. When the shape and color of the colony surface are observed, a light pink hypha mass is formed in the colony. If a plurality of hypha masses are formed within the colony which has grown concentrically from the site of inoculation, the hypha masses are interconnected by mycelial strands. The color of the back of the colony is light pink.

When this organism is cultured on a glucose-dry yeast agar medium, cultured hyphae have clamps, and are smooth, but form no conidia, and form no fruit bodies. When the shape and color of the colony surface are observed, light pink to white hypha masses are formed in the colony. Hypha masses of 5 to 6 mm in thickness are formed, with the site of inoculation as a center. The color of the back of the colony is light pink to white.

The optimum growth conditions for the organism of the present invention are, for example, pH 5.0 to 6.0 and a temperature of 22 to 26° C. The growth range is, for example, pH 4.0 to 7.5 and a temperature of 5 to 30° C.

Basidiomycetes, the organism according to the present invention, can be cultured by an ordinary method, and the method of its culture is not limited.

The Basidiomycetes extract composition of the present invention may be any cell contents extracted from hypha masses obtained by culturing Basidiomycetes, and the method of extraction is not limited. To extract cell contents from the hypha masses with high efficiency, it is preferred to damage cell walls, for example, by freezing of the hypha masses, if desired, thaw the frozen masses, and then crush them by means of a mixer or the like, followed by extraction. The method of extraction is not limited, but extraction is performed at room temperature, or under heating conditions, or under pressure, with the use of water, a lower alcohol or the like, or an extraction solution further incorporating an acid, an alkali or other additive. Generally, the crushed product is simmered in hot water for extraction, or the crushed product mixed with water or alcohol, or water incorporating an alkali is extracted under pressure, for example, of the order of 100 MPa to 700 MPa, preferably, 300 MPa to 600 MPa.

An example of extraction in hot water will be described. For example, frozen Basidiomycetes-X hypha masses are thawed at room temperature, and crushed using a mixer. The ratio of the crushed Basidiomycetes-X hypha masses to water as an extraction solvent is set, for example, at 1:5. For example, 50 g of the crushed Basidiomycetes-X hypha masses are placed in a glass bottle, 250 ml of water is added, and the glass bottle is covered with a lid. A towel is spread at the bottom of a pan, water is poured over the towel, and the glass bottle filled with the crushed hypha masses is placed on the towel, followed by heating and boiling. After boiling, heating is continued for 90 minutes. After cooling, the solids and liquid are separated to obtain a Basidiomycetes-X extract. The pH of the extract shows, for example, 6.3 to 6.5.

The resulting extract is concentrated, where necessary, to obtain a Basidiomycetes extract composition. Concentration of the extract is not limited, but is performed, for example, in the following manner:

The resulting Basidiomycetes-X extract is transferred into a beaker, and heated and evaporated for concentration. At this time, the extract shows a light beige to brown color, and begins to bubble vigorously. However, evaporation and concentration are continued further, and concentration is completed, for example, at a time when the concentrated extract becomes tarry at pH 4.9 and a density of 1.25 g/cm$^3$. The concentrated extract gives off a soy sauce-like odor. The yield of the concentrated extract from the Basidiomycetes-X hypha masses at this point in time is an average of 12%.

The thus obtained concentrated extract becomes very viscous as it cools. Thus, the concentrated extract needs to be transferred into a storage container at the same time as the completion of concentration. The concentrated extract transferred into the storage container is preferably cooled as it is, and then stored in a refrigerated or frozen state.

The Basidiomycetes extract composition of the present invention can be used in health foods or medicines, such as immunopotentiators, in the form of, for example, drinks, snacks, concentrated extract, powder, granules, tablets, or capsules. The amount of the Basidiomycetes extract composition added may be set, as appropriate, in accordance with uses, and is not limited.

Furthermore, hypha masses obtained by culturing Basidiomycetes, which is the organism according to the present invention, can be used for eating purposes, and are excellent in taste and organoleptic sensation.

The Basidiomycetes of the present invention, when cultured, forms hypha masses in accordance with an environment where it is cultured. That is, when the Basidiomycetes is cultured in a vessel of a predetermined shape, hypha masses of the shape of the vessel are obtained. Thus, edible Basidiomycetes easy to use for eating purposes is obtained. The resulting edible Basidiomycetes may be used raw as a food material, or may be used in a frozen or dried state as a food material, but preferably, is used as a raw material or a frozen material.

In connection with the method of culture, the Basidiomycetes can be cultured by an ordinary method as stated earlier, and the culture method is not limited. For example, however, an agar medium, a sawdust medium, or a liquid medium, which has been supplemented with a suitable nutrient source and sterilized, is aseptically inoculated with a cultured strain of the invented organism, or the seed organism, and the inoculum is cultured under appropriate temperature conditions, whereby hypha masses of Basidiomycetes-X can be obtained.

The method of cooking the edible Basidiomycetes used as a food material is not limited. However, the edible Basidiomycetes can be cooked in the same various ways as for ordinary mushrooms, such as simmering, pan-frying, roasting, and deep-frying, without any limitations. Since the edible Basidiomycetes gives an excellent organoleptic sensation and does not taste characteristically, it can be used widely in various prepared foods.

Eating the edible Basidiomycetes is, needless to say, assumed to obtain the same effect as when eating the Basidiomycetes extract composition.

EXAMPLES

The present invention will now be described more concretely with reference to the examples offered below. Examples 1 to 4 represent cultivation examples of Basidiomycetes-X, and Examples 5 to 9 represent extraction examples.

Example 1

Separation from Hypha Masses (1) Preparation of Culture Media

PSA and PDA culture media were prepared in accordance with the formulations shown in Table 1. Each of the culture media was dispensed into test tubes or Erlenmeyer flasks. Then, silicon caps (or cotton stoppers) were applied, and the stoppered containers were subjected to high pressure steam sterilization in an autoclave for 20 minutes at 121° C. Then, the test tubes were inclined while hot after sterilization to form slant media. On the other hand, the Erlenmeyer flasks were allowed to stand to form plate media.

TABLE 1

| PSA culture medium | PDA culture medium |
|---|---|
| Extract of 200 g of potatoes boiled for 20 minutes | Extract of 200 g of potatoes boiled for 20 minutes |
| 20 g sucrose | 20 g glucose |
| 15 g agar | 15 g agar |
| Total amount 1 liter | Total amount 1 liter |

(2) Separation from Hypha Masses

Larger Basidiomycetes-X hypha masses were broken manually, and slices were cut from Basidiomycetes-X sections with a scalpel which had been flame sterilized and cooled. The PDA and PSA slant media of (1) were each inoculated with the Basidiomycetes-X slices using tweezers which had been flame sterilized and cooled. This procedure was performed under aseptic conditions within an aseptic box or a clean bench.

(3) Culture

The inoculum was cultured in an incubator at 24° C., and found to generate the organism in 24 to 48 hours. After generation of the organism, culture was continued at 24° C. Hyphae grew on the agar media in 14 days.

Example 2

Culture on Sawdust Medium for Hypha Mass Production (1) Culture of Seed Organism Water was added to 1 liter of sawdust, 15 g of defatted bran, 15 g of wheat bran, and 5 g of SANPEARL (hypha activator, Nippon Paper Industries), and the mixture was vigorously stirred. This mixture for culture was adjusted such that when it was firmly gripped, water exuded (moisture content of the mixture: about 70%), whereby a sawdust medium was prepared. This culture medium was placed in an Erlenmeyer flask, which was covered with a silicon cap. Then, the Erlenmeyer flask was subjected to high pressure steam sterilization in an autoclave for 40 minutes at 121° C. Twenty-four hours after the sterilization, Basidiomycetes-X hyphae during culture on the slant media in Example 1 were inoculated into the sawdust medium within an aseptic box by an aseptic operation. The inoculation was carried out such that no damage was caused to the hyphae, with a sterilized triangular knife being used to cut off a part of the slant medium. The density of the inoculation was 20 to 30% of the surface area of the sawdust medium. When the inoculum was cultured at 24° C., the organism was generated in 3 days (in 5 days at the latest). After a lapse of 30 days, the sawdust medium in the Erlenmeyer flask was full of the organism.

(3) Generation of Hypha Masses

A sawdust medium was prepared in the same manner as in (1). This culture medium was placed in a polypropylene bottle, which was stoppered, and subjected to high pressure steam sterilization in an autoclave for 40 minutes at 121° C. Twenty-four hours after the sterilization, the seed organism cultured in (1) was inoculated into the sawdust medium in the polypropylene bottle by an aseptic operation within an aseptic box after aseptic treatment. The density of the inoculation was such that the surface area of the sawdust medium was nearly covered with the inoculum. When the inoculum was cultured at 24° C., the organism was generated in 48 hours. After a lapse of 60 days, the entire sawdust medium within the polypropylene bottle was full of hyphae. After a further lapse of 40 to 50 days, hyphae spread on the inner wall of the polypropylene bottle, forming mycelial strands. When culture was continued further, hypha masses were formed.

Example 3

Culture on Liquid Medium for Hypha Mass Production

Potatoes (200 g) cut to a size of 1 cm square were boiled using purified water, followed by heating for 20 minutes. After cooling, the solids and the liquid were separated, and distilled water was added to the resulting potato leachate and 20 g of sucrose to give a total amount of 1 liter, thereby preparing a liquid medium. This liquid medium was dispensed in an amount of 5 ml each into test tubes. The test tubes were covered with silicon caps, and sterilized (high-pressure steam sterilization for 20 minute at 121° C. or atmospheric pressure steam sterilization for 8 hours at 100° C.). Then, the liquid media were inoculated by an aseptic operation within an aseptic box after aseptic treatment such that the lower ends of slices of Basidiomycetes-X during culture on the slant media in Example 1 contacted the liquid media. When the inoculum was cultured at 24° C., the organism was generated in 48 hours. Upon further culture, hypha masses were formed in contact with the liquid media.

Example 4

Culture on Agar Medium for Hypha Mass Production

Potatoes (200 g) cut to a size of 1 cm square were boiled using purified water, followed by heating for 20 minutes. After cooling, the solids and the liquid were separated, and distilled water was added to the resulting potato leachate, 20 g of sucrose, and 1 g (0.1%) agar to give a total amount of 1 liter, thereby preparing an agar medium. Normally, to prepare an agar medium, 1.5 to 2.0% of agar (15 to 20 g based on 1 liter of the resulting medium) is added, but 0.1% of agar was added to facilitate separation of hypha masses after culture and the agar medium, and also to maintain the physical strength of the liquid medium because slices of Basidiomycetes-X tend to settle out in the liquid medium. This 0.1% agar medium was dispensed in an amount of 5 ml each into test tubes. The test tubes were covered with silicon caps, and then subjected to high pressure steam sterilization for 20 minute at 121° C. Then, slices were cut from Basidiomycetes-X hypha masses during culture on the slant media in Example 1, and inoculated into the 0.1% agar media by an aseptic operation within an aseptic box after aseptic treatment. When the inoculum was cultured at 24° C., the organism was generated in 48 hours. Upon further culture, hypha masses were formed.

Example 5

Production of Concentrated Basidiomycetes-X Extract Composition by Decoction

To cause damage to the cell walls of the hyphae and facilitate the leaching-out of the cell contents, fresh Basidiomycetes-X hypha masses were refrigerated or frozen. The frozen Basidiomycetes-X hypha masses were thawed at room temperature, and crushed using a mixer. The crushed Basidiomycetes-X hypha masses (50 g) were placed in a glass bottle, 250 ml of water was added, and the glass bottle was covered with a lid. A towel was spread at the bottom of a pan, water was poured over the towel, and the glass bottle filled with the crushed hypha masses was placed on the towel, followed by heating and boiling. After boiling, heating was continued for 90 minutes. After cooling, the solids and liquid were separated to obtain a Basidiomycetes-X extract composition. The pH of the extract was 6.3 to 6.5.

The resulting Basidiomycetes-X extract composition was transferred into a beaker, and concentrated upon heating and evaporation. The extract composition showed a light beige to brown color, and began to bubble vigorously. However, evaporation and concentration were continued further, and concentration was completed at a time when the concentrated extract composition became tarry at pH 4.9 and a density of 1.25 $g/cm^3$. The concentrated Basidiomycetes-X extract composition gave off a soy sauce-like odor. The yield of the concentrated Basidiomycetes-X extract composition from the Basidiomycetes-X hypha masses at this point in time was an average of 12%. The Basidiomycetes-X extract composition becomes very viscous as it cools. Thus, simultaneously with the completion of concentration, the concentrate was transferred into a storage container and, after cooling, was stored as such in a refrigerated or frozen state.

Example 6

Production of Basidiomycetes-X Extract Composition by Decoction

To cause damage to the cell walls of the hyphae and facilitate the leaching-out of the cell contents, fresh Basidiomycetes-X hypha masses were refrigerated or frozen. Then, the frozen Basidiomycetes-X hypha masses were thawed at room temperature.

The Basidiomycetes-X hypha masses (wet weight 20 g) after thawing were weighed, cut to a size of 0.5 cm square, and placed in a beaker. After 100 ml of water was added, the contents of the beaker were cooked gently at 90° C., and the solution was boiled down to a half of the original amount. Then, water was added to restore the original amount. The mixture was filtered through a gauze to remove the solids. Then, the filtrate was sealed up, and stored in a refrigerator for use as a Basidiomycetes-X extract composition of Example 6.

Example 7

Production of Basidiomycetes-X Extract Composition by High Pressure Treatment

The Basidiomycetes-X hypha masses (wet weight 20 g) treated in the same manner as in Example 6 were taken into a vinyl bag, and 100 ml of water was added. Then, the vinyl bag was deaerated under reduced pressure, and sealed. The vinyl bag was set in an ultra-high pressure apparatus (a product of Kobe Steel; capable of treatment at 700 MPa), and treated for 10 minutes at a hydrostatic pressure of 400 MPa. The treated mixture was filtered through a gauze, and the filtrate was stored in a refrigerated state for use as a Basidiomycetes-X extract composition of Example 7.

Example 8

Production of Basidiomycetes-X Extract Composition by High Pressure Treatment

A composition produced in the same manner as in Example 7, except for treatment at a hydrostatic pressure of 600 MPa, was put to use as a Basidiomycetes-X extract composition of Example 8.

Example 9

Production of Basidiomycetes-X Extract Composition by High Pressure Treatment

A composition produced in the same manner as in Example 8, except for the use of 100 ml of a 0.1% KCl aqueous solution instead of 100 ml of water, was put to use as a Basidiomycetes-X extract composition of Example 9.

Test Example 1

Measurement of Active Oxygen (Hydroxy Radicals) Elimination Activity

The activity of eliminating hydroxy radicals was measured by ESR (electron spin resonance) using $H_2O_2$/UV as a hydroxy radical generation source, and dimethylpyrroline-N-oxide (DMPO) as a spin trapper.

DMPO (40 mM) and 20 mM of hydrogen peroxide were added to a constant amount of the Basidiomycetes-X extract composition in each of Examples 6 to 9, and purified water was added to give a total amount of 300 µl. The mixture was irradiated with UV (band width 20 nm) at a wavelength of 245 nm, and the resulting hydroxy radical addition product of DMPO was observed for ESR signals. Based on changes in the intensity of the signals, the hydroxy radical elimination activity of the extract composition was determined. The results are shown in FIG. 1.

As shown in FIG. 1, the larger the amount of the Basidiomycetes-X extract composition, the higher the elimination rate of the hydroxy radicals became. Example 7, which involved extraction by high pressure treatment at 400 MPa in a water solvent, obtained the highest hydroxy radical elimination rate.

Test Example 2

Measurement of Active Oxygen (Superoxide Anion Radicals) Elimination Activity

The activity of eliminating superoxide anion radicals was measured by ESR (electron spin resonance) in accordance with the spin-trap method using a xanthine-xanthine oxidase system as a superoxide anion radical generation system, and DMPO as a spin trapper.

DMPO (0.3 mM), 0.5 mM of hypoxanthine, and 1 mM of diethylenetriaminepentaacetic acid (DTPA) were added to a constant amount of the Basidiomycetes-X extract composition in each of Examples 6 to 9, and 0.2M PBS was added to give a total amount of 300 µl. Xanthine oxidase was added in a concentration of 0.1 unit/ml, and the resulting DMPO-OOH (superoxide anion radical addition product of DMPO) was observed for ESR signals. Based on changes in the intensity of the signals, the elimination activity of the extract composition was determined. The results are shown in FIG. 2.

Figure 2:
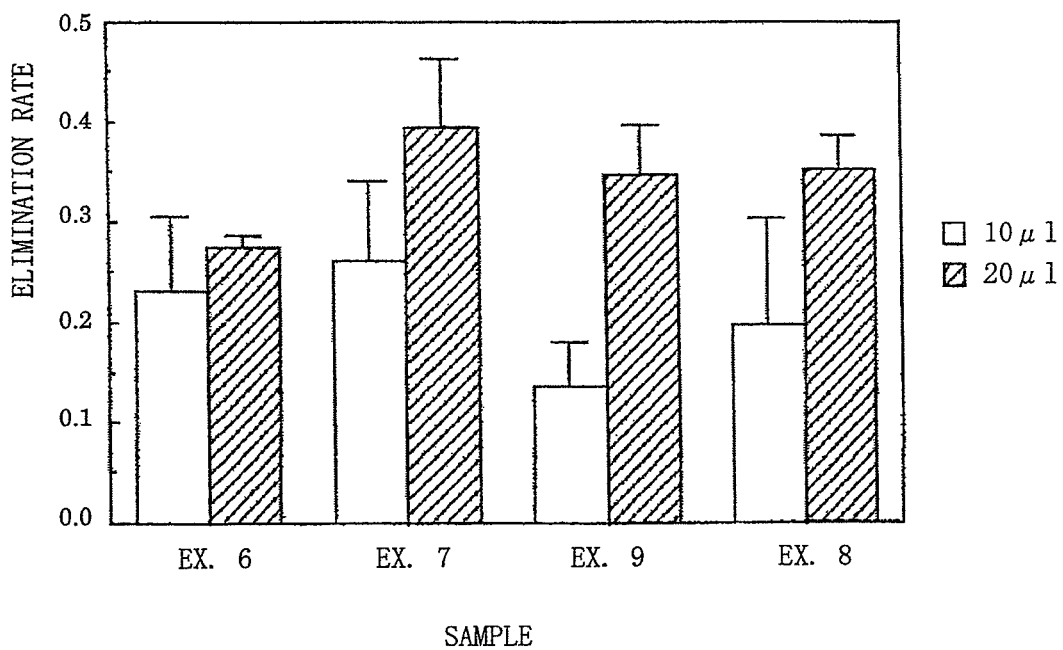
FIG. 2 is a view showing the results of measurements in Test Example 2.

As shown in FIG. 2, the larger the amount of the extract composition, the higher the elimination rate of the superoxide anion radicals became. Example 7, which involved extraction by high-pressure treatment at 400 MPa in a water solvent, obtained the highest superoxide anion radical elimination rate. These results were similar to those in Test Example 1.

Test Example 3

Measurement of Active Oxygen (Hydroxy Radicals) Elimination Activity

The activity of eliminating hydroxy radicals was measured by the ESR spin-trap method using Fenton reaction as a hydroxy radical generation source, and DMPO as a spin trapper.

Dimethylpyrroline N-oxide (DMPO) (20 mM), 10 mM of hydrogen peroxide, and 0.1 mM of $FeSO_4$ were added to a constant amount (10 or 20 µl) each of an extract obtained by decocting and extracting dried agaricus (a product of Truffle Japan) under the same conditions as in Example 6, an extract obtained by decocting and extracting dried reishi mushroom (*Ganoderma lucidum* (Leyss. ex Fr.) Karst.; a product of Truffle Japan) under the same conditions as in Example 6, and the Basidiomycetes-X extract composition in each of Examples 6 to 9. Purified water was further added to give a total amount of 300 µl, and the resulting mixture was used as an assay sample. Based on changes in the intensity of the signals of DMPO-OH (a hydroxy radical addition product of DMPO) one minute after addition of $FeSO_4$, the elimination activity was determined. The results are shown in FIG. 3.

Figure 3:
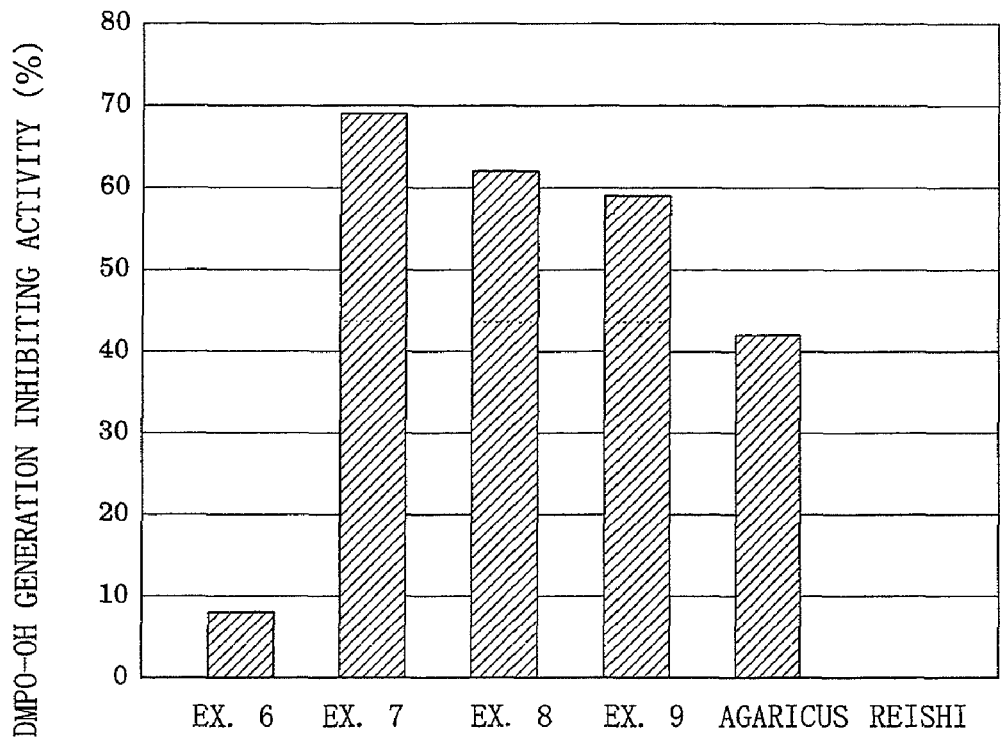
FIG. 3 is a view showing the results of measurements in Test Example 3.

As shown in FIG. 3, Example 6, which involved extraction by decoction, was not successful in estimating detailed elimination activity, because the extract of Example 6, when at a low concentration, interacted with iron ions as did the reishi mushroom extract, and caused increases in, rather than the elimination of, DMPO-OH signals. When the extract of Example 6 was used at a high concentration minimal in influence on the signals, and was compared with the other extracts, the extract of Example 6 showed comparable elimination activity to that of the agaricus extract. Examples 7 to 9 involving extraction by high pressure treatment gave higher elimination activity than did agaricus and reishi mushroom.

Test Example 4

Measurement of Immunomodulating Effect

Mice used were C3H/HeJ mice of CLEA Japan. C3H/HeJ mice show deteriorated immunity when elderly. In the present study, "retirees" (20 to 30 week old) were used as elderly mice. The concentrated Basidiomycetes-X extract composition of Example 5 was used as Basidiomycetes-X. For this assay, Associate Professor Akira Yanagawa, Applied Pharmacology Lab., 3rd Dept., Institute of Medical Science, St. Marianna Univ. School of Medicine cooperated, and performed work unpaid.

The retiree mice were divided into groups of 10 mice, and allocated to a Basidiomycetes-X treatment group administered the concentrated Basidiomycetes-X extract composition in a dose of 0.2 ml once daily, and a control group receiving 0.2 ml physiological saline once daily. The Basidiomycetes-X or physiological saline was administered orally for 14 consecutive days using a stomach tube.

Figure 4:
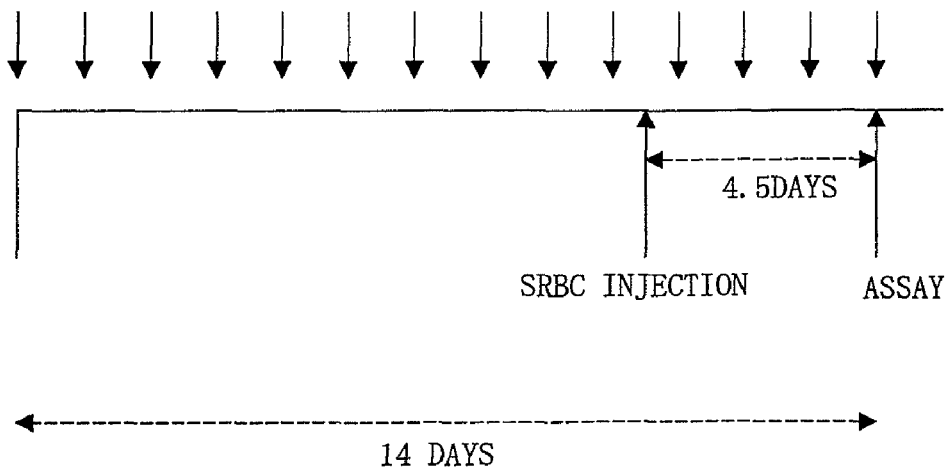
FIG. 4 is a schematic view showing the mode of administration in Test Example 4.
Figure 5:
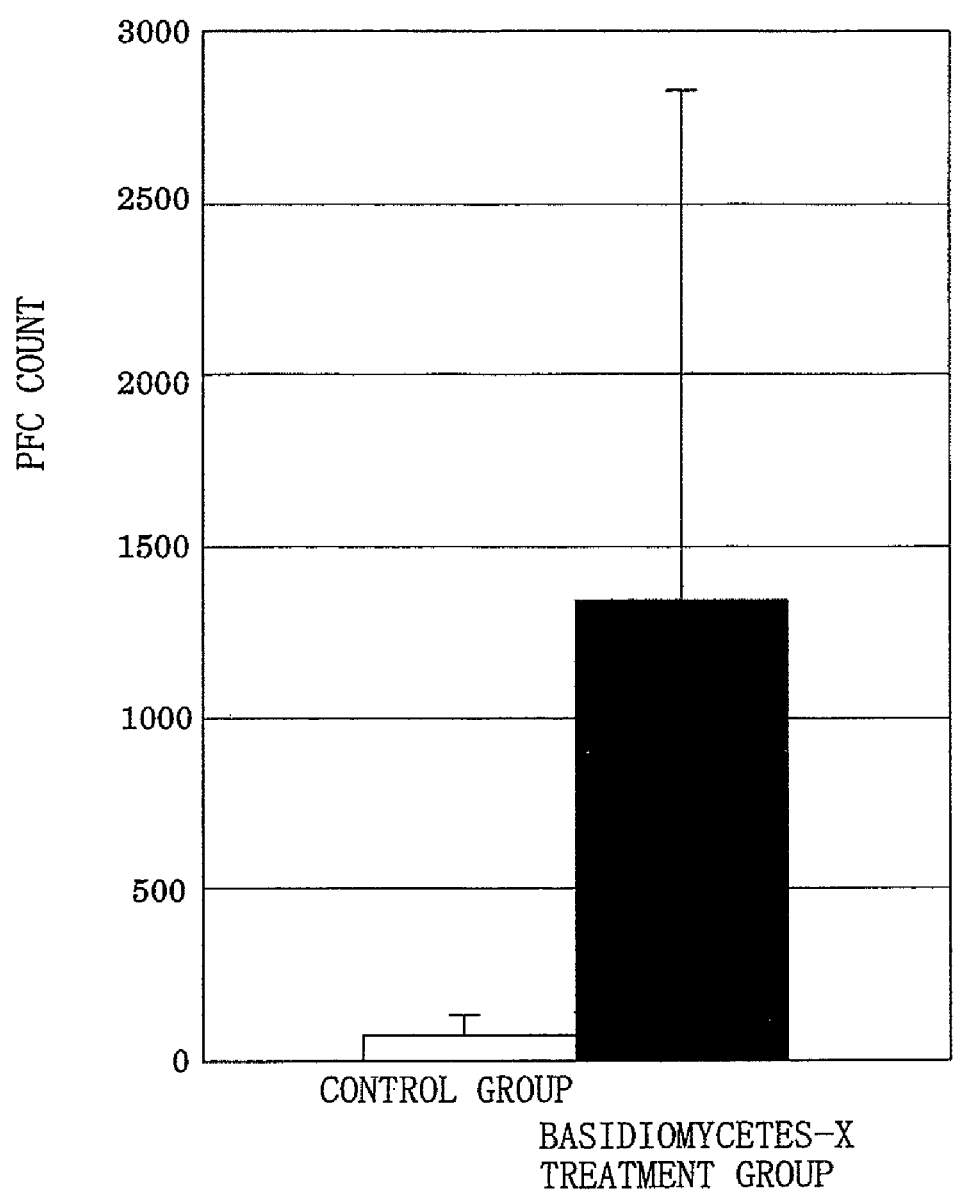
FIG. 5 is a view showing the results of measurements in Test Example 4.

Ten days after initiation of the treatment, 0.1 ml of 10% sheep red blood cells (SRBC) diluted with phosphate buffered physiological saline (PBS) (i.e., cell count $2\times10^8$) was administered intraperitoneally to the mice. After a lapse of 4.5 days, mouse splenic cells were removed, and the number of plaque forming cells (PFC) was counted by the method of Jerne. The PFC count was compared with that in the control group. The results of measurement of the PFC count in the control group are shown in Table 2, and the results of measurement of the PFC count in the Basidiomycetes-X treatment group are shown in Table 3. A schematic view of the modes of administration of Basidiomycetes-X or physiological saline, and SRBC is shown in FIG. 4. The results of assay are shown in FIG. 5.

TABLE 2

| No. | Cell count in cell suspension ($\times 10^6$ cells/ml) | Cell suspension seeded into Petri dish (ml) | PFC (/Petri dish) | PFC (/$10^6$ cells) Individual | Mean | SD |
|---|---|---|---|---|---|---|
| 1 | 31 | 0.2 | 0 | 0 | | |
| 2 | 51.25 | 0.03 | 10.33 | 6.72 | | |
| 3 | 59.75 | 0.03 | 198.98 | 110.98 | | |
| 4 | 53.65 | 0.03 | 150.68 | 93.59 | | |
| 5 | 76.15 | 0.03 | 162.54 | 71.13 | | |
| | | | | | 75.399 | 62.98075 |
| 6 | 42 | 0.2 | 0 | 0 | | |
| 7 | 62.65 | 0.03 | 148.76 | 79.13 | | |
| 8 | 26.25 | 0.03 | 126.36 | 160.36 | | |
| 9 | 38.25 | 0.03 | 203.42 | 177.12 | | |
| 10 | 63.45 | 0.03 | 104.64 | 54.96 | | |

*PFC/Petri dish ÷ (cell suspension seeded into Petri dish × cell count in cell suspension) = PFC individual

TABLE 3

| No. | Cell count in cell suspension ($\times 10^6$ cells/ml) | Cell suspension seeded into Petri dish (ml) | PFC (/Petri dish) | PFC (/$10^6$ cells) Individual | Mean | SD |
|---|---|---|---|---|---|---|
| 1 | 20 | 0.03 | 263.33 | 438.88 | | |
| 2 | 30.75 | 0.2 | 8078.4 | 1077.12 | | |
| 3 | 55.25 | 0.2 | 4125.6 | 373.36 | | |

TABLE 3-continued

| No. | Cell count in cell suspension (×10$^6$) cells/ml) | Cell suspension seeded into Petri dish (ml) | PFC (/Petri dish) | PFC (/10$^6$ cells) Individual | Mean | SD |
|---|---|---|---|---|---|---|
| 4 | 41.5 | 0.03 | 483 | 387.95 | | |
| 5 | 32 | 0.03 | 565.33 | 588.89 | | |
| | | | | | 1345.9 | 1495.324 |
| 6 | 43.5 | 0.03 | 826.34 | 633.21 | | |
| 7 | 62 | 0.2 | 6236.42 | 502.9 | | |
| 8 | 53.45 | 0.03 | 7326.6 | 4567.77 | | |
| 9 | 36.5 | 0.2 | 9236.6 | 1265.53 | | |
| 10 | 79.75 | 0.03 | 8672 | 3626.39 | | |

As shown in Tables 2 and 3, the Basidiomycetes-X treatment group showed the PFV value of 1345.9 and the SD value of 1495.324, which were about 20 times those in the control group showing the PFC mean value of 75.399 and the SD value of 62.98075. Two-sided test according to equal distribution in Student T test showed Basidiomycetes-X to increase the PFC count significantly at P=0.023363 (p<0.05).

The experiments of the present study demonstrated the concentrated Basidiomycetes-X extract composition to increase the PFC count significantly in comparison with the physiological saline in the control group. The PFC experimental method using C3H/HeJ mice is the method commonly practiced as a standard screening method for testing the immunomodulating potential. The increase in the PFC count in the aged mice showed that the concentrated Basidiomycetes-X extract composition enhances compromised immunocompetence.

Test Example 5

Course of Immunocompetence Parameters in Cancer Patients

The course of immunocompetence parameters in cancer patients (case 1 to case 6) was monitored during treatment with the concentrated Basidiomycetes-X extract composition of Example 5 to investigate the immunopotentiating effect of the concentrated Basidiomycetes-X extract composition. For this study, Associate Professor Akira Yanagawa, Applied Pharmacology Lab., 3rd Dept., Institute of Medical Science, St. Marianna Univ. School of Medicine, cooperated, and performed work unpaid.

Concretely, 1 ml of purified water was added to 1 ml of the concentrated Basidiomycetes-X extract composition, and the mixture was orally administered 3 times daily, after each meal. This treatment lasted for 3 weeks.

As immunocompetence parameters, BML (BML, Inc.) was asked to measure the following items before and after treatment on a blind basis. The results are shown in Tables 4 to 15. The six patients with cancer were all different in the primary lesion of cancer. Since it bears no meaning to calculate the mean value of these six patients, the values of the individual patients were enumerated.

As NK cells:
  Two color (as activity evaluation of NK cells)
    CD57+CD16+(%) NK activity moderate
    CD57+CD16−(%) NK activity weak
    CD57−CD16+(%) NK activity strong
    CD57−CD16−(%)
As total activated NK cell count:
  CD3+HLA−DR+(%) Activated CD3 cells Besides, the leukocyte count, the lymphocytes (%) and lymphocyte count in the leukocyte differential count were also measured. Furthermore, the cooperative patients were requested to enter in diaries changes in symptoms during treatment.

(Case 1) In July 2000, total sigmoidectomy was performed for sigmoid colon cancer. In 2002, recurrent carcinoma was confirmed during operation for parietal cicatricial hernia. Then, ileus frequently occurred.

TABLE 4

NK cell system
Two color (activity evaluation of NK cells)

| | Before treatment (lymphocyte count: LC) | After treatment (LC) |
|---|---|---|
| CD57+CD16+ (%) NK activity moderate | 6.6% (149) | 8.0% (250) |
| CD57+CD16− (%) NK activity weak | 17.6% (396) | 17.6% (549) |
| CD57−CD16+ (%) NK activity strong | 4.6% (104) | 4.1% (128) |
| CD57−CD16− (%) | 71.2% | 70.3% |

TABLE 5

As total activated NK cell count

| | Before treatment (lymphocyte count: LC) | After treatment (LC) |
|---|---|---|
| CD3+HLA−DR+ (%) Activated CD3 cells | 9.9% (223) | 10.6% (331) |

In case 1, the lymphocytes having moderate and weak NK cell activity were markedly increased as compared with the pretreatment levels. The CD57−CD16+ cells having strong NK activity showed the post-treatment value of 4.1%, apparently indicating a decrease in %. However, the actual count of lymphocytes increased from 104 to 128. In regard to the CD3+HLA−DR+cells as an object of assay for the entire profile of NK cells, the post-treatment value was 10.6% (331), showing an increase over the pretreatment value of 9.9% (223).

(Case 2) Total resection of left breast cancer was performed in October 1999. Then, the carcinoma relapsed, and has currently metastasized to the lung, bone, brain, and meninx. Even after radiotherapy for meningeal dissemination, cranial nerve paralysis made the patient bedridden. Spinal cord metastasis also caused progressive right upper limb paralysis. The systemic condition is severely poor for terminal cancer.

TABLE 6

NK cell system
Two color (as activity evaluation of NK cells)

| | Before treatment (lymphocyte count: LC) | After treatment (LC) |
|---|---|---|
| CD57+CD16+ (%) NK activity moderate | 12.6% (136) | 9.4% (111) |
| CD57+CD16− (%) NK activity weak | 5.76% (62) | 6.8% (80) |
| CD57−CD16+ (%) NK activity strong | 9.4% (102) | 7.0% (83) |
| CD57−CD16− (%) | 72.3% | 76.8% |

TABLE 7

As total activated NK cell count

|  | Before treatment (lymphocyte count: LC) | After treatment (LC) |
| --- | --- | --- |
| CD3+HLA–DR+ (%) Activated CD3 cells | 5.7% (62) | 3.6% (43) |

In case 2, the influence of the concentrated Basidiomycetes-X extract composition on NK cells was not observed.

(Case 3) In August 2001, mucinous cystadenocarcinoma and bilateral metastatic ovarian tumor necessitated resection. Then, carcinomatous peritoneal dissemination and carcinomatous inflammation resulted in large amounts of ascitic retention. Currently, the patient is bedridden because of terminal cancer.

TABLE 8

NK cell system
Two color (as activity evaluation of NK cells)

|  | Before treatment (lymphocyte count: LC) | After treatment (LC) |
| --- | --- | --- |
| CD57+CD16+ (%) NK activity moderate | 5.5% | 5.8% |
| CD57+CD16– (%) NK activity weak | 21.8% | 16.0% |
| CD57–CD16+ (%) NK activity strong | 7.7% | 6.8% |
| CD57–CD16– (%) | 65.0% | 71.4% |

TABLE 9

As total activated NK cell count

|  | Before treatment (lymphocyte count: LC) | After treatment (LC) |
| --- | --- | --- |
| CD3+HLA–DR+ (%) Activated CD3 cells | 15.5% | 13.1% |

In Case 3, a slight increase in CD57+CD16+ lymphocytes having moderate NK activity was observed.

(Case 4) In 2001, chemotherapy and radiotherapy were performed for pulmonary carcinoma (squamous cell carcinoma, T2N3M0). Then, an operation for total resection of the left lung was performed. In 2002, metastatic brain tumor (cerebral metastasis of lung cancer) necessitated metastatic brain tumor resection. However, multiple cerebral metastasis occurred as a complication in the same year.

TABLE 10

NK cell system
Two color (as activity evaluation of NK cells)

|  | Before treatment (lymphocyte count: LC) | After treatment (LC) |
| --- | --- | --- |
| CD57+CD16+ (%) NK activity moderate | 5.3% | 2.6% |
| CD57+CD16– (%) NK activity weak | 1.1% | 0.6% |
| CD57–CD16+ (%) NK activity strong | 8.8% | 5.9% |
| CD57–CD16– (%) | 84.8% | 90.9% |

TABLE 11

As total activated NK cell count

|  | Before treatment (lymphocyte count: LC) | After treatment (LC) |
| --- | --- | --- |
| CD3+HLA–DR+ (%) Activated CD3 cells | 5.2% | 4.7% |

In this patient, the NK cell increasing effect of the concentrated Basidiomycetes-X extract composition was not observed.

(Case 5) In October 2001, lung cancer (adenocarcinoma) was noted. At diagnosis, metastasis to the right cervical lymph node was observed, and metastasis to the hilar lymph nodes was complicated by superior vena cava syndrome. Therapies included 60 Gy radiation of the right neck regions and chemotherapy (CBDCA+TAy 4 courses). The superior vena cava remained completely obstructed, and carcinomatous pleuritis concomitantly occurred. The medications were frequently given in the pulmonary cavity, but decreased the lesion only mildly. In addition, metastasis to the brain was recently confirmed upon CT.

TABLE 12

NK cell system
Two color (as activity evaluation of NK cells)

|  | Before treatment (lymphocyte count: LC) | After-treatment (LC) |
| --- | --- | --- |
| CD57+CD16+ (%) NK activity moderate | 12.1% (256) | 17.5% (431) |
| CD57+CD16– (%) NK activity weak | 36.5% (773) | 44.6% (1099) |
| CD57–CD16+ (%) NK activity strong | 4.3% (91) | 6.0% (148) |
| CD57–CD16– (%) | 47.0% | 31.9% |

TABLE 13

As total activated NK cell count

|  | Before treatment (lymphocyte count: LC) | After treatment (LC) |
| --- | --- | --- |
| CD3+HLA–DR+ (%) Activated CD3 cells | 22.2% (469) | 32.3% (796) |

In the present case, all the NK cell parameters were increased, and the oral administration of the concentrated Basidiomycetes-X extract composition increased NK cell activity and the number of NK cells. This case is evaluated as a case of excellent response.

(Case 6) In July 2002, gastric cancer (Borrmann type I gastric carcinoma in the gastric vestibule) was found. However, the patient did not wish for an operation, and fell into the state of terminal cancer.

TABLE 14

NK cell system
Two color (as activity evaluation of NK cells)

|  | Before treatment (lymphocyte count: LC) | After treatment (LC) |
| --- | --- | --- |
| CD57+CD16+ (%) NK activity moderate | 30.1% | 30.9% |

TABLE 14-continued

NK cell system
Two color (as activity evaluation of NK cells)

|  | Before treatment (lymphocyte count: LC) | After treatment (LC) |
|---|---|---|
| CD57+CD16− (%) NK activity weak | 7.8% | 7.1% |
| CD57−CD16+ (%) NK activity strong | 6.2% | 6.7% |
| CD57−CD16− (%) | 55.9% | 55.3% |

TABLE 15

As total activated NK cell count

|  | Before treatment (lymphocyte count: LC) | After treatment (LC) |
|---|---|---|
| CD3+HLA−DR+ (%) Activated CD3 cells | 9.9% | 9.1% |

In the present case, CD57−CD16+(%) (NK activity strong) and CD57+CD16+(%) (NK activity moderate) were increased.

Even among terminal cancer patients., two types are present, patients who can still live the usual daily life, and bedridden patients in the terminal stage. The concentrated Basidiomycetes-X extract composition, when ingested, was expected to obtain a marked effect of enhancing immunity (increasing NK cells) even in the former patients, i.e., patients with terminal cancer, who can live a daily life. On the other hand, some relationship was suspected between pathological findings of cancer and the concentrated Basidiomycetes-X extract composition. In patients with adenocarcinomas, such as case 1 of colon cancer (adenocarcinoma), case 3 of mucinous cystadenocarcinoma (a type of adenocarcinoma), case 5 of pulmonary cancer (adenocarcinoma) and case 6 of gastric carcinoma (adenocarcinoma), some moves were observed in NK cell parameters after treatment with the concentrated Basidiomycetes-X extract composition. However, case 4 was likewise a case of pulmonary cancer, but was pathologically diagnosed as having squamous cell carcinoma. In this patient, the concentrated Basidiomycetes-X extract composition exerted no influence on any of the NK dynamic parameters.

Test Example 6

Course of Immunocompetence Parameters in Cancer Patients (8 Months of Treatment)

In case 3 and case 1 of Test Example 5, a mixture of 1 ml of the concentrated Basidiomycetes-X extract composition and 1 ml of purified water was orally administered 3 times daily, after each meal, in succession to Test Example 5. The course of immunological parameters after more than 6 months of treatment is shown in Tables 16 and 17.
(Case 3)

TABLE 16

|  | Before treatment (lymphocyte count: LC) | After 3 weeks of treatment (LC) | After 8 months of treatment (LC) |
|---|---|---|---|
| WBC count | 3,100 | 3,000 | 2,900 |
| RBC count | 3,420,000 | 3,340,000 | 3,430,000 |
| Hb | 11.6 | 11.1 | 10.4 |
| Ht | 34.7 | 33.5 | 32.6 |
| CD57+CD16+ (%) NK activity moderate | 5.5% | 5.8% | 3.1% |
| CD57+CD16− (%) NK activity weak | 21.8% | 16.0% | 13.4% |
| CD57−CD16+ (%) NK activity strong | 7.7% | 6.8% | 5.3% |
| CD3+HLA−DR+ (%) Activated CD3 cells | 15.5% | 13.1% | 31.6% |

In the present patient, moderate to strong NK activity was exhibited as terminal cancer progressed.

Lymphocytes gradually decreased. On the other hand, activated lymphocytes were not markedly changed after 3 weeks of treatment, but increased to 31.6% in 8 months. Thus, increases in lymphocytes (activated) similar to those after LAK (lymphokine activated killer) therapy were observed.
(Case 1)

TABLE 17

|  | Before treatment (lymphocyte count: LC) | After 3 weeks of treatment (LC) | After 8 months of treatment (LC) |
|---|---|---|---|
| WBC count | 7,800 | 7,500 | 14,400 |
| RBC count | 4,170,000 | 3,720,000 | 3,760,000 |
| Hb | 11.5 | 10.1 | 9.1 |
| Ht | 35.0 | 30.5 | 28.9 |
| CD57+CD16+ (%) NK activity moderate | 6.6% (149) | 8.0% (250) | 5.0% |
| CD57+CD16− (%) NK activity weak | 17.6% (396) | 17.6% (549) | 26.6% |
| CD57−CD16+ (%) NK activity strong | 4.6% (104) | 4.1% (128) | 2.9% |
| CD3+HLA−DR+ (%) Activated CD3 cells | 9.9% (223) | 10.6% (331) | 22.7% |

In the present patient, CD57+CD16+ with moderate NK activity increased after 3 weeks of oral administration. Moreover, CD57+CD16− cells with weak NK activity increased after 8 months of oral administration. In addition, the activated CD3 cells increased to 10.6% at 3 weeks of treatment, and to 22.7% after 8 months of treatment.

In conclusion, NK activity slightly increased after treatment in comparison with that before treatment.

The finding worthy of notice was that CD3+HLA−DR+ cells, markers of activated T lymphocytes, remarkably increased after oral administration. This outcome is normally observed after LAK therapy and, without doubt, is considered to be the extraordinary outcome of the Basidiomycetes-X extract composition.

In patients receiving long-term treatment with the Basidiomycetes-X extract composition, marked increases in activated lymphocytes similar to those after LAK therapy were observed, although this was the outcome in 2 patients. Based on this finding, further study seems to be necessary in an increased number of patients. However, the Basidiomycetes-X extract composition was suggested to have the potential of increasing activated T lymphocytes and directing the immune system toward exclusion of cancer in patients with terminal cancer.

Example 10

Foods were cooked in accordance with the following recipes using edible Basidiomycetes. In all foods, the organoleptic sensation of edible Basidiomycetes was satisfactory, and its taste was good and went well with the foods.

1. Pasta

Just boiled pasta and sliced edible Basidiomycetes are lightly pan-fried in olive oil. Then, the mixture is preferredly seasoned with a seasoning such as salt or pepper. Once the edible Basidiomycetes is cooked through, the food is ready.

2. Pizza

Slices of raw edible Basidiomycetes are arranged on pizza dough, cheese is sprinkled, and this combination is baked in an oven. Once cheese is melted uniformly, the food is ready.

3. Deep-Fried Seasoned Meat or Fish

Chicken or fish is preliminarily seasoned with soy sauce or seasoning sweet sake. The pre-seasoned chicken or fish is sprinkled with *Erythronium japonicum* starch, and slightly soaked in beaten eggs. Then, sliced raw edible Basidiomycetes is evenly pressed against the chicken or fish, and the thus treated chicken or fish is deep-fried in oil. Once the edible Basidiomycetes becomes crisp, the food is ready.

4. Omelet

Eggs are beaten, and seasoned in the desired manner with a seasoning such as salt or pepper. Finely cut raw edible Basidiomycetes is added, followed by further stirring. Then, the beaten eggs with the other material are poured into a frying pan hot enough for an oil to smoke lightly. The beaten eggs are agitated so as not to become solid, and the flame is turned down. While the surface of the eggs is solidified with the remaining heat of the frying pan, the egg material is rolled. When it is golden brown on the surface, and half-done inside, the food is ready.

INDUSTRIAL APPLICABILITY

As described above, the present invention can provide Basidiomycetes which is a novel mushroom having an excellent immunopotentiating action, a Basidiomycetes extract composition, health foods and immunopotentiators using the Basidiomycetes extract composition, and edible Basidiomycetes.

Mention of Microorganism
Name of Deposition Organ: International Patent Organism Depositary, National Institute of Advanced Industrial Science and Technology
Address of Deposition Organ: Chuo Dai-6, Higashi 1-1-1, Tsukuba City, Ibaragi Prefecture, Japan (postal code 305-8566)
Date of Deposition with Deposition Organ: Feb. 27, 2003
Accession Number Assigned by Deposition Organ at Deposition: FERM BP-10011
Name of Depositor: Y. Tsuno, Representative Director, Mycology Techno Kabushiki Kaisha
Address of Depositor: Bandai 4-3-20, Niigata City, Niigata Prefecture, Japan (postal code 950-0088)
The deposited microorganism was domestically deposited on Feb. 27, 2003 with International Patent Organism Depositary, National Institute of Advanced Industrial Science and Technology (Accession No.: FERM P-19241), and transferred to international deposition (Accession No.: FERM BP-10011) on Apr. 15, 2004.

Other information on the features of the microorganism
Type of the microorganism: Mold
Place in taxonomy: Basidiomycetes, sclerotium (hypha mass) unidentified in species
Culture conditions:
  Name of culture medium . . . Potato glucose agar medium
  Composition of culture medium . . . Leachate of 200 g of potatoes, 20 g glucose, 20 g agar per 1000 mL of the culture medium
  pH of culture medium . . . 5.6
  Sterilization conditions for culture medium: 121° C., 20 minutes in autoclave
  Culture temperature . . . 24° C.
  Culture period . . . 5 days
  Requirement for oxygen . . . Aerobic
  Culture method . . . Aerobic
  Requirement for light . . . Unnecessary
  Subculture conditions . . . Transfer interval 3 months, storage temperature 5° in cool dark place
Storage conditions:
  Storage by freeze-drying . . . Negative
  Storage by L-drying . . . Negative
  Storage by freezing (around −80° C.) . . . Negative
  Storage if the above methods are unavailable . . . Storage by subculture (transfer interval 3 months, storage temperature 5° in cool dark place)
Spore (conidium) formation: None

The invention claimed is:

1. A Basidiomycetes extract composition comprising a solvent extract of a hyphal mass of the strain Basidiomycetes-X FERM BP-10011 wherein said extract has medicinal properties.

2. The Basidiomycetes extract composition of claim 1, wherein the solvent is hydrophilic.

3. The Basidiomycetes extract composition of claim 1, wherein the solvent is water.

4. The Basidiomycetes extract composition according to claim 2, wherein the Basidiomycetes extract composition is obtained by heating the extract.

5. The Basidiomycetes extract composition according to claim 2, wherein the Basidiomycetes extract composition is obtained by pressurization of the extract.

6. The Basidiomycetes extract composition according to claim 4, wherein the Basidiomycetes extract composition is obtained by pressurization of the extract.

7. A health comprising the Basidiomycetes extract composition of claims 1 and foodstuff.

8. The health food according to claim 7, wherein the foodstuff is a drink, a snack, a concentrate.

9. The Basidiomycetes extract composition of claim 1 wherein the extract has a immunomodulating effect.

10. The health food of claim 8, wherein the food stuff is in the form of a powder, granule, tablet or capsule.

* * * * *